United States Patent [19]

Suzuki et al.

[11] Patent Number: 5,980,926
[45] Date of Patent: Nov. 9, 1999

[54] WATER DISPERSIBLE GRANULE

[75] Inventors: Masahiro Suzuki, Shizuoka; Michio Tani, Himimachi; Keiichi Sato, Shizuoka, all of Japan

[73] Assignee: Nippon Soda Co., Ltd., Tokyo, Japan

[21] Appl. No.: 09/011,427

[22] PCT Filed: Jun. 6, 1997

[86] PCT No.: PCT/JP97/01923

§ 371 Date: Feb. 10, 1998

§ 102(e) Date: Feb. 10, 1998

[87] PCT Pub. No.: WO97/46093

PCT Pub. Date: Dec. 11, 1997

[30] Foreign Application Priority Data

Jun. 7, 1996 [JP] Japan .................................. 8-166675

[51] Int. Cl.$^6$ .......................... A01N 25/00; A01N 43/78; A01N 43/50; A01N 47/28
[52] U.S. Cl. .......................... 424/405; 514/365; 514/385; 514/399; 514/584; 514/587
[58] Field of Search .............................. 504/116; 514/618, 514/619, 621, 622, 613, 399, 385, 365, 584, 587; 424/405

[56] References Cited

U.S. PATENT DOCUMENTS

| | | | |
|---|---|---|---|
| 4,844,734 | 7/1989 | Iwasaki et al. | 71/120 |
| 5,045,109 | 9/1991 | Nakamura et al. | 71/100 |
| 5,232,701 | 8/1993 | Ogawa et al. | 424/408 |
| 5,264,213 | 11/1993 | Shibahara et al. | 424/409 |
| 5,728,649 | 3/1998 | Hasebe et al. | 504/116 |

FOREIGN PATENT DOCUMENTS

| | | |
|---|---|---|
| 0689866 | 1/1996 | France . |
| 4305501 | 10/1992 | Japan . |
| 5017303 | 1/1993 | Japan . |

*Primary Examiner*—Jose' G. Dees
*Assistant Examiner*—Alton Pryor
*Attorney, Agent, or Firm*—Joseph C. Mason, Jr.

[57] ABSTRACT

A granular hydrating agent having an excellent dispersibility wherein a tristyryl phenyl ether, with polyoxyethylene added thereto, as a dispersant and a dispersion aid are incorporated at the time of wet pulverization to improve the capability of granulation and at least one member selected among sodium alkylnaphthalenesulfonates and sodium alkylbenzenesulfonates and a dispersion aid are incorporated at the time of dilution.

4 Claims, No Drawings

WATER DISPERSIBLE GRANULE

This application is a 371 of PCT/JP97/01923, filed Jun. 6, 1997.

FIELD OF THE INVENTION

The present invention relates to a water dispersible granule.

BACKGROUND ART

Active ingredient components useful as a pesticide, such as insecticides, fungicides and herbicides, have been prepared into formulations, such as wettable powders and dusts, depending upon their physicochemical properties and the objective to use them practically in agricultural crop fields. A wettable powder and a dust can be formulated by admixing a solid active component useful as a pesticide, inorganic mineral carriers and surface active agents and subsequently allowing the mixture to a process of dry milling. The particle size is in a range of from 5 to 10 μm, so there is a problem of securing safety on human bodies, such as powder inhalation problem at the time of measuring a powder formulation to dilute with water. In order to solve such problem as described above, a water dispersible granule which is manufactured according to extrusion method has been developed recently.

The water dispersible granule produced according to the extrusion method is manufactured by admixing a solid active component useful as a pesticide, a carrier composed of mineral fine powder, a surfactant, etc., adding bound water after the dry milling process, kneading by using a kneader, and subsequently forcing the kneaded-material to pass through a plate having holes with a diameter of from 0.5 to 1.0 mm.

However, the production of the water dispersible granule by means of dry milling process could not be made in cases that the pesticidal active component has a low melting point and therefore it is not suitable for the dry milling, or in case that it is necessary to further allow the active substance to a fine milling in order to enhance its biological activity.

Therefore, when producing the water dispersible granule according to the extrusion method where a pesticidal active component either having a low melting point and therefore not being applicable for dry milling process or being required to be subjected to fine pulverization process for enhancing its biological activity, it was necessary in the past to allow the active substance to wet millimg process and then to kneading granulation process in combination with a carrier composed of mineral materials.

On the other hand, from the same purpose as described above, a method to firstly make the active substance to a slurry state by means of wet milling process, then to mix the slurry with a carrier of minerals and finally to allow the mixture to the extrusion process to obtain granules has been developed. For example, in Japanese Patent Laid-open No. Hei 3-146126 Gazette, a method to improve the dispersibility at milling and the granulation property by adding a small amount of sodium alkylnaphthalenesulfonate during the process of wet milling is disclosed. However, there is still a problem that wet milling of the active substance might be not possible sometime depending upon the chemical property of the active substance itself, due to the lowering of dispersibility of sodium alkylnaphthalenesulfonate.

DISCLOSURE OF THE INVENTION

In case of wet milling, it is not possible to obtain a suspension wherein a pesticidal active component with required particle size is dispersed therein because of the flocculation of the suspension to be likely caused if such pesticidal active component does not have enough affinity to water and is not completely dispersible in water. Basing on this reason, an appropriate surfactant functionable as a dispersing agent is frequently used in the wet milling process. However, the surfactant does not always give an excellent dispersibility to the active components, and thereby some pesticidal components may cause the flocculation in the suspension. Therefore, it is an object of the present invention to provide a water dispersible granule suitable for preparing the formulations of pesticides, which may secure good dispersibility of pesticidal component without flocculation during wet milling process, having good granulation property, and provides good suspension stability of the pesticidal component in the dilution.

The present invention is directed to a water dispersible granule containing 0.01–30% by weight of a pesticidal component relative to the weight of the whole water dispersible granule, and comprising 0.1–10% by weight of tristyryl phenyl ether added thereon with polyoxyethylene, 1–10% by weight of either or both a sodium alkylnaphthalenesulfonate and/or a sodium alkylbenzenesulfonate, 1–40% by weight of a dispersion aid and 1–50% by weight of carrier mineral powder, relative to the weight of the whole water dispersible granule, and a method for the preparation of the water dispersible granule constituted with the following processes, (1) a process to combine a pesticidal component which is in solid at an ambient temperature and is hardly-soluble in water, tristyryl phenyl ether added thereon with polyoxyethylene and a dispersion aid, and to allow the combination obtained to wet milling process, (2) a process to admix carrier mineral powder, either or both a sodium alkylnaphthalenesulfonate and/or a sodium alkylbenzenesulfonate, and a dispersion aid, and (3) a process to mix the mixture obtained in the process (1) into the mixture obtained in the process (2) and then to allow the resulting mixture to the extrusion process.

Any pesticide which is in solid at an ambient temperature, is hardly-soluble in water and preferably has a solubility in water as much as 1,000 ppm, can be used as the pesticidal component usable in the present invention without any limitation, and more than 2 pesticidal components may be used in combination. For the example of the pesticidal component to be used in the present invention, triflumizole, thiuram, fluazinam, anilazine, captan, hexythiazox, benzoximate, tebufenpyrad, ziram, thiophanate-methyl and benzamideixime compounds represented by a general formula (1);

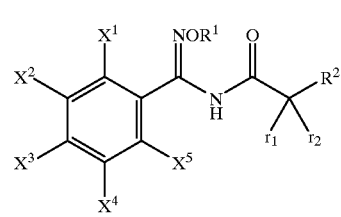

(I)

wherein
R$^1$ is optionally substituted C$_1$–C$_4$ alkyl, optionally substituted C$_2$–C$_4$ alkenyl or optionally substituted C$_2$–C$_4$ alkynyl,
R$^2$ is optionally substituted phenyl or optionally substituted heterocycle, $X^1$ is $C_1$–$C_4$ haloalkyl, $X^2$, $X^3$, $X^4$ and $X^5$ are each independently hydrogen, a halogen atom, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, nitro, amino or $C_1$–$C_4$ alkylcarbonylamino, $r_1$ and $r_2$ are each independently hydrogen, a halogen atom, $C_1$–$C_4$ alkyl, $C_1$–$C_4$ haloalkyl, $C_1$–$C_4$ alkoxy, $C_1$–$C_4$ alkylthio or amino, or $r_1$ and $r_2$ may jointly form a carbonyl group, which are disclosed in WO96/19442 Gazette by the applicant of the present invention, can be given.

Definitive examples for the compounds represented by the general formula [I] are shown in Table 1.

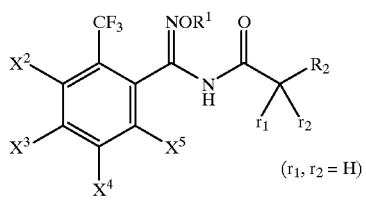

($r_1$, $r_2$ = H)

| No. | $X_2$ | $X_3$ | $X_4$ | $X_5$ | $R_1$ | $R_2$ |
|---|---|---|---|---|---|---|
| 1 | H | H | F | F | $CH_2$—△ | Ph |
| 2 | H | H | Cl | F | $CH_2$—△ | Ph |
| 3 | H | H | F | Cl | $CH_2$—△ | Ph |
| 4 | H | H | Cl | Cl | $CH_2$—△ | Ph |
| 5 | H | H | F | F | $CH_2$—△ | 2-F—Ph |
| 6 | H | H | Cl | F | $CH_2$—△ | 2-F—Ph |
| 7 | H | H | F | Cl | $CH_2$—△ | 2-F—Ph |
| 8 | H | H | Cl | Cl | $CH_2$—△ | 2-F—Ph |
| 9 | H | H | F | F | $CH_2$—△ | 2-F-5-Me—Ph |
| 10 | H | H | Cl | F | $CH_2$—△ | 2-F-5-Me—Ph |
| 11 | H | H | F | Cl | $CH_2$—△ | 2-F-5-Me—Ph |
| 12 | H | H | Cl | Cl | $CH_2$—△ | 2-F-5-Me—Ph |
| 13 | H | H | F | F | $CH_2CH_2Cl$ | Ph |

-continued

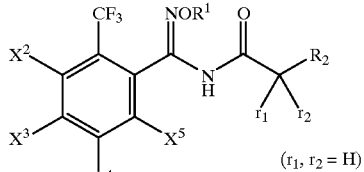

($r_1$, $r_2$ = H)

| No. | $X_2$ | $X_3$ | $X_4$ | $X_5$ | $R_1$ | $R_2$ |
|---|---|---|---|---|---|---|
| 14 | H | H | Cl | F | $CH_2CH_2Cl$ | Ph |
| 15 | H | H | F | Cl | $CH_2CH_2Cl$ | Ph |
| 16 | H | H | Cl | Cl | $CH_2CH_2Cl$ | Ph |
| 17 | H | H | F | F | $CH_2CH_2Cl$ | 2-F—Ph |
| 18 | H | H | Cl | F | $CH_2CH_2Cl$ | 2-F—Ph |
| 19 | H | H | F | Cl | $CH_2CH_2Cl$ | 2-F—Ph |
| 20 | H | H | Cl | Cl | $CH_2CH_2Cl$ | 2-F—Ph |
| 21 | H | H | F | F | $CH_2CH_2Cl$ | 2-F-5-Me—Ph |
| 22 | H | H | Cl | F | $CH_2CH_2Cl$ | 2-F-5-Me—Ph |
| 23 | H | H | F | Cl | $CH_2CH_2Cl$ | 2-F-5-Me—Ph |
| 24 | H | H | Cl | Cl | $CH_2CH_2Cl$ | 2-F-5-Me—Ph |

In the present invention, as the tristyryl phenyl ether added thereon with polyoxyethylene to be combined at the wet milling operation in the first process, it is preferable to use the one added thereon with ethylene oxide in an amount of 9–60 mols and having HLB of from 12 to 15.

Further, it is also allowable to use more than 2 of such tristyryl phenyl ether added thereon with polyoxyethylene in combination. This tristyryl phenyl ether added thereon with polyoxyethylene is incorporated as a dispersing agent at the time of the wet milling operation.

In the present invention, as the examples of the dispersion aid to be incorporated at the time of wet milling in the first process, sodium ligninsulfonate, formaldehyde condensates of sodium alklnaphthalenesulfonate, isobutylene-maleic anhydride copolymer, sodium polycarboxylate and the like are given, and these products can be used either alone of in a form of the mixture comprising more than 2 of them.

In the present invention, the sodium alkylnaphthalenesulfonates, the sodium alkylbenzenesulfonates and the like, which are incorporated in the second process, are used as a dispersing agent for using at granulation improvement process and dilution process, and they can be used either alone or by mixing of more than 2 of them.

In the present invention, as the example of the dispersion aid to be incorporated in the second process, sodium ligninsulfonate, formaldehyde condensates of sodium alkylnaphthalenesulfonates, isobutylene-maleic anhydride copolymer, sodium polycarboxylate and the like are given, and these products can be used either alone or by mixing of more than 2 of them.

In the present invention, as the examples of the carrier mineral powder to be incorporated in the second process, potassium chloride, an inorganic calcium salt such as calcium carbonate, diatomaceous earth, pyrophyllite-type clay, kaolinite-type clay and the like are given, and these products can be used either alone or by mixing of more than 2 of them.

In the present invention, in order to minimize foaming produced at the time of wet milling and dilution, any of a silicon-type surfactant, a sodium salt or a calcium salt of a higher fatty acid or the mixture thereof, an acetylene-type surfactant and the like can be added to the water dispersible granule according to the present invention.

The normal rates for the incorporation of each components in the water dispersible granule according to the present invention, as the rate relative to the whole weight of the water dispersible granule, are 0.01–30% by weight and preferably 0.01–20% by weight for a pesticidal component, 0.1–10% by weight and preferably 0.5–3% by weight for tristyryl phenyl ether added thereon with polyoxyethylene, 1–10% by weight and preferably 0.5–3% by weight for a sodium alkylnaphthalensulfonate, 1–10% by weight and preferably 0.5–3% by weight for a sodium alkylbenzenesulfonate, 1–10% by weight and preferably 1–5% by weight for a dispersion aid for using at wet milling, 1–30% by weight and preferably 5–20% by weight for a dispersion aid for using at dilution, 1–50% by weight and preferably 10–40% by weight for a carrier mineral powder, and 5% by weight or less and preferably 3% by weight or less for a defoamer, respectively.

The water dispersible granule of the present invention (hereinafter referred to as WDG, if appropriate) can be prepared according to the following procedure. In this procedure, tristyryl phenyl ether added thereon with polyoxyethylene, a dispersion aid and a defoamer are dissolved or dispersed in water, and the solution obtained is then allowed to wet milling process to prepare a suspension to be used for the water dispersible granule (hereinafter referred to as WDG-SC, if appropriate). Then, a sodium alkylnaphthalenesulfonate, a sodium alkylbenzenesulfonate, a dispersion aid and a carrier mineral powder are admixed and then allowed to dry milling process to prepare a wettable powder to be used for the water dispersible granule (hereinafter referred to as WDG-WP, if appropriate). Then, WDG-SC is added to WDG-WP, and the mixture obtained is then added with water and further allowed to kneading process using a kneader. The kneaded product is then passed through a porous plate to obtain wet granules in noodle shape and the granules is dried by using an appropriate dryer to prepare the water dispersible granule according to the present invention.

BEST MODE FOR CARRYING OUT THE INVENTION

EXAMPLES

Now, the present invention is further described in detail with referring to the examples disclosed hereinbelow, however, it should be noted that the present invention is not limited to the scope as defined by the following examples.

Example 1

Triflumizole in an amount of 110 g, tristyryl phenyl ether added thereon with ethylene oxide of which HLB being about 15 in an amount of 10 g, sodium polycarboxylate in an amount of 10 g and a silicon-containing defoamer in an amount of 2.5 g are admixed and added with distilled water in an amount of 200 g, and the mixture is uniformly dissolved and dispersed by using Polytron. The suspension obtained was then allowed to wet milling process by using Eiger Motor Mill (Produced by Eiger Japan K.K.) wherein zircon beads with a diameter of 1 mm are used to prepare WDG-SC which contains triflumizole with a average particle size of 1.5 μm. A sodium alkylnaphthalenesulfonate in an amount of 20 g, a sodium alkylbenzenesulfonate in an amount of 20 g, a formaldehyde condensate of sodium ligninsulfonate in an amount of 70 g, diatomaceous earth in an amount of 300 g and potassium chloride in an amount of 317.5 g are admixed and then allowed to dry milling process using a horizontal jet mill (Diameter: 3.5 inches) to prepare WDG-WP. WDG-WP in an amount of 867.5 g was then added with WDG-SC obtained above in an amount of 332.5 g and water in an amount of 143 g, and the mixture obtained was allowed to kneading process using Bench Kneader (Produced by Irie Shokai K.K.). The kneaded product was then put into a micro-type granulating machine (Produced by Tsutsui Rikagaku Kikai K.K.) to prepare wet noodle-shaped granules with a diameter of 0.6 mm, and the granules were then dried at 40° C. for 12 hours under a fan dryer to obtain WDG.

Example 2

Thiophanate-methyl in an amount of 160 g, tristyryl phenyl ether added thereon with ethylene oxide of which HLB being about 15 in an amount of 20 g, sodium polycarboxylate in an amount of 10 g and a silicon-containing defoamer in an amount of 2.5 g are admixed and added with distilled water in an amount of 300 g, and the mixture is then allowed to wet milling process after taking the same procedure as described in the example 1 to prepare WDG-SC which contains thiophanate-methyl with a average particle size of 1.0 μm. A sodium alkylnaphthalenesulfonate in an amount of 40 g, a sodium alkylbenzenesulfonate in an amount of 140 g, sodium ligninsulfonate in an amount of 70 g, diatomaceous earth in an amount of 400 g and potassium chloride in an amount of 157.5 g are admixed and then allowed to dry milling process according to the same procedure described in the example 1 to prepare WDG-WP. WDG-WP in an amount of 807.5 g was then added with WDG-SC obtained above in an amount of 492.5 g and water in an amount of 200 g, and the mixture obtained was allowed to further processes as described in the example 1 to obtain WDG.

Example 3

Hexythiazox in an amount of 110 g, tristyryl phenyl ether added thereon with ethylene oxide of which HLB being about 15 in an amount of 10 g, sodium polycarboxylate in an amount of 10 g and a silicon-containing defoamer in an amount of 2.5 g are admixed and added with distilled water in an amount of 200 g, and the mixture is then allowed to wet milling process after taking the same procedure as described in the example 1 to prepare WDG-SC which contains hexythiazox with a average particle size of 1.0 μm. A sodium alkylnaphthalenesulfonate in an amount of 30 g, a sodium alkylbenzenesulfonate in an amount of 10 g, a formaldehyde condensate of a sodium alkylnaphthalenesulfonate in an amount of 140 g. sodium ligninsulfonate in an amount of 70 g, diatomaceous earth in an amount of 300 g and potassium chloride in an amount of 317.5 g are admixed and then allowed to dry millimg process according to the same procedure described in the example 1 to prepare WDG-WP. WDG-WP in an amount of 867.5 g was then added with WDG-SC obtained above in an amount of 332.5 g and water in an amount of 140 g, and the mixture obtained was allowed to further processes as described in the example 1 to obtain WDG.

Example 4

The compound (No.1) represented by the general formula [I] in an amount of 110 g, tristyryl phenyl ether added thereon with ethylene oxide of which HLB being about 15 in an amount of 10 g, sodium polycarboxylate in an amount of 10 g and a silicon-containing defoamer in an amount of 2.5 g are admixed and added with distilled water in an amount of 200 g, and the mixture is then allowed to wet milling process after taking the same procedure as described in the example 1 to prepare WDG-SC which contains a pesticidal component with an average particle size of 1.5 μm. A sodium alkylnaphthalenesulfonate in an amount of 25 g, a sodium alkylbenzenesulfonate in an amount of 20 g, a formaldehyde condensate of a sodium alkylnaphthalene-sulfonate in an amount of 140 g, sodium ligninsulfonate in an amount of 70 g, diatomaceous earth in an amount of 300 g and potassium chloride in an amount of 312.5 g are admixed and then allowed to dry milling process according to the same procedure described in the example 1 to prepare WDG-WP. WDG-WP obtained in an amount of 867.5 g was then added with WDG-SC prepared above in an amount of 332.5 g and water in an amount of 140 g, and the mixture obtained was allowed to further processes as described in the example 1 to obtain WDG.

Reference Example 1

The compound (No.1) represented by the general formula [I] in an amount of 110 g, a sodium alkylnaphthalene-sulfonate in an amount of 40 g, sodium polycarboxylate in an amount of 20 g and a silicon-containing defoamer in an amount of 2.5 g are admixed and added with distilled water in an amount of 200 g, and the mixture is then allowed to wet milling process after taking the same procedure as described in the example 1. However, it was not possible to mill the mixture because of causing the flocculation of a pesticidal component.

Reference Example 2

The compound (No.1) represented by the general formula [I] in an amount of 110 g, a sodium alkylnaphthalene-sulfonate in an amount of 40 g, sodium ligninsulfonate in an amount of 70 g and a silicon-containing defoamer in an amount of 2.5 g are admixed and added with distilled water in an amount of 200 g, and the mixture is then allowed to wet milling process after taking the same procedure as described in the example 1. However, it was not possible to mill the mixture because of causing the flocculation of a pesticidal component.

Reference Example 3

The compound (No.1) represented by the general formula [I] in an amount of 110 g, a sodium alkylnaphthalene-sulfonate in an amount of 40 g, a formaldehyde condensate of a sodium alkylnaphthalenesulfonate in an amount of 70 g and a silicon-containing defoamer in an amount of 2.5 g are admixed and added with distillated water in an amount of 200 g, and the mixture is then allowed to wet milling process after taking the same procedure as described in the example 1. However, it was not possible to mill the mixture because of causing the flocculation of a pesticidal component.

Industrial Use:

The present invention is directed to a water dispersible granule particularly suitable for pesticidal active components which cannot be allowed to dry milling process due to their low melting points and is required to be milled to fine powder in order to enhance their biological activity. According to the present invention, the water dispersible granule suitable for preparing pesticide formulations which can disperse pesticidal components without causing their flocculation during wet milling process, provides good granulation property and has excellent suspension stability of the pesticidal component in the dilution.

What is claimed is:

1. A water dispersible granule containing a pesticidal component, consisting essentially of 0.01%–30% by weight of the pesticidal component, 0.1%–10% by weight of tristyryl phenyl ether added thereon with polyoxyethylene, 1%–10% by weight of a sulfonate selected from the group consisting of sodium alkylnaphthalenesulfonate and sodium alkylbenzensulfonate, 1%–40% of a dispersion aid and 1%–50% by weight of a mineral powder carrier.

2. The water dispersible granule of claim 1 wherein the mineral powder carrier is selected from the group consisting of inorganic salt, diatomaceous earth, pyrophyllite-type clay and kaolinite-type clay.

3. The water dispersible granule of claim 1 wherein the pesticidal component is selected from the group consisting of triflumizole, thiophanate-methyl, hexythiazox and a benzamidoxime compound having the structural formula:

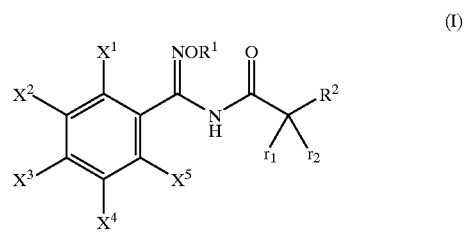

(I)

wherein $R^1$ is optionally substituted $C_1$–$C_4$ alkyl, optionally substituted $C_2$–$C_4$ alkenyl or optionally substituted $C_2$–$C_4$ alkynyl, $R^2$ is optionally substituted phenyl, $X^1$ is $C_1$–$C_4$ haloalkyl, $X^2$, $X^3$, $X^4$ and $X^5$ are each independently hydrogen, a halogen atom, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ alkysulfinyl, $C_1$–$C_4$ alkysufonyl, nitro, amino or $C_1$–$C_4$ alkycarbonylamino, $r_1$ and $r_2$ are each independently hydrogen, a halogen atom, $C_1$–$C_4$ alkyl, $C_1$–$C_4$ haloalkyl, $C_1$–$C_4$ alkoxy, $C_1$–$C_4$ alkylthio or amino, or $r_1$ and $r_2$ may jointly form a carbonyl group.

4. A method of making a water dispersible granule containing a pesticidal component consisting essentially of the steps of:

(a) admixing 0.01%–30% by weight of the pesticidal component which is a solid at ambient temperature and is insoluble in water with
  (i) 0.1%–10% by weight of tristyryl phenyl ether added thereon with polyoxyethylene,
  (ii) 1%–40% by weight of a dispersion aid, and
  (iii) water to form a solution thereof;

(b) subjecting the solution to a wet milling process to reduce the solid pesticidal component to a powder form;

(c) then, separately, admixing 1%–50% by weight of a mineral powder carrier, 1%–10% by weight of a sulfonate selected from the group consisting of sodium alkylnaphthalenesulfonate and sodium alkylbenzenesulfonates, and 1%–40% by weight of the dispersion aid;

(d) thereafter, subjecting the admixture to a dry milling process;

(e) next, adding the mixture obtained from the wet milling process of step (b) to the admixture obtained from the dry milling process of step (d); and (f) thereafter subjecting the mixture obtained from step (e) to extrusion treatment whereby granules containing the powdered pesticidal component are obtained.

* * * * *